United States Patent [19]

Ringhardtz

[11] 4,443,104
[45] Apr. 17, 1984

[54] FLUORIMETER SAMPLING APPARATUS

[75] Inventor: Ingo Ringhardtz, Überlingen, Fed. Rep. of Germany

[73] Assignee: The Perkin-Elmer Corporation, Norwalk, Conn.

[21] Appl. No.: 341,386

[22] Filed: Jan. 21, 1982

[30] Foreign Application Priority Data

Mar. 6, 1981 [DE] Fed. Rep. of Germany ....... 3108474

[51] Int. Cl.³ .............................................. G01N 1/10
[52] U.S. Cl. ................................. 356/246; 250/461.2
[58] Field of Search ........................ 356/244, 246, 339; 250/576, 461.2; 422/63, 65, 102, 104

[56] References Cited

U.S. PATENT DOCUMENTS

| 3,695,772 | 10/1972 | Spyropoulos | 356/246 |
| 3,854,050 | 12/1974 | Peterson et al. | 250/461.2 X |
| 4,013,368 | 3/1977 | Acker et al. | 356/246 |
| 4,060,388 | 11/1977 | Rapp et al. | 356/246 X |
| 4,325,910 | 4/1982 | Jordan | 356/218 X |

Primary Examiner—William L. Sikes
Assistant Examiner—Matthew W. Koren
Attorney, Agent, or Firm—F. L. Masselle; E. T. Grimes; R. A. Hays

[57] ABSTRACT

A fluorimeter sampling apparatus useful in a fluorimeter includes a linearly movable sample carrier having a plurality of cuvette holders associated therewith. Each cuvette holder, when positioned in a measuring position, is aligned with an excitation radiation entrance aperture and a fluorescence radiation exit aperture. The cuvette holders are diagonally aligned with the direction of movement of the carrier.

4 Claims, 3 Drawing Figures

FLUORIMETER SAMPLING APPARATUS

BACKGROUND OF THE INVENTION

The present invention generally relates to an apparatus useful for presenting samples to the exitation radiation of a fluorimeter and, in particular, relates to an apparatus including a linearly movable carrier.

Conventionally, a fluorimeter sampling apparatus includes a turntable having cuvette receptacles arranged on a circular line near the periphery thereof. To present samples, the turntable is rotated about its axis within a sample housing whereby the sample-containing cuvettes in the cuvette receptacles are individually and successively positioned in a measuring position. In this arrangement, the exitation radiation enters the housing along a radius of the turntable into the cuvette in the measuring position. The resultant fluorescence radiation exits in a direction normal with respect to the exitation radiation and is subsequently measured by a fluorimeter positioned external to the housing.

However, the above-described apparatus includes an inherent limitation on the number of samples which can be included on a single turntable. This limitation is significant as the number of samples to be measured increases, for example, in fluorescence-immuno assays, the processing of large numbers of samples is commonplace. The turntable apparatus is unsuited for such large numbers of samples since, if the radius is enlarged to accommodate more samples, the entire apparatus, including the housing, becomes quite bulky. Further, there is a practical limit to the number of samples usable on a given turntable due to the required geometrical arrangement of the optical paths within the housing.

SUMMARY OF THE INVENTION

Accordingly, it is one object of the present invention to provide a fluorimeter sampling apparatus that is adapted for the serial investigation of a large number of samples.

This object is achieved, at least in part, by means of a linearly movable carrier, which carrier includes a cuvette holder releasably attached thereto. In one embodiment, the cuvette holder comprises a generally rectangular base plate with a plurality of cuvettes arranged diagonally with respect to the longitudinal axis of the base plate and with retaining means for connecting the base plate to the carrier.

Such a linear arrangement of the cuvettes in the direction of the carrier displacement permits a relatively large number of cuvettes to be successively and individually positioned in the measuring position without blocking the path of the relevant light rays. The adaptation of the carrier to linear displacement makes the apparatus particularly suitable for automation.

Other objects and advantages will become apparent from the following detailed description and the accompanying drawings

BRIEF DESCRIPTION OF THE DRAWING

The drawing, which is not drawn to scale, includes.

DETAILED DESCRIPTION OF THE INVENTION

Figure 2:
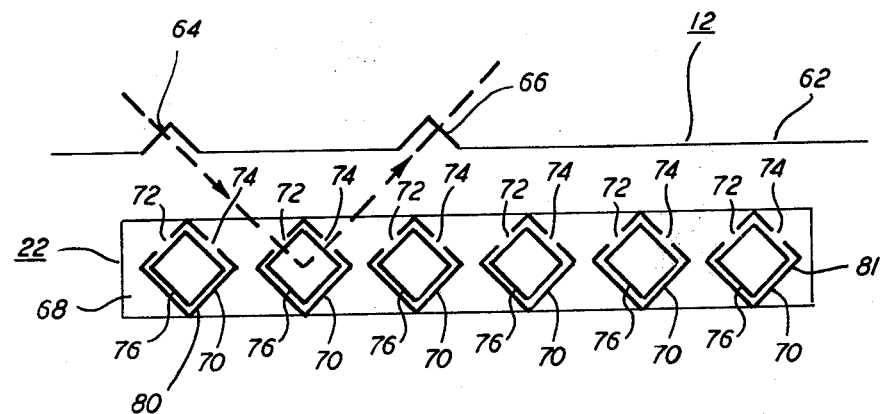
FIG. 2, which is a schematic plan view of one embodiment of a cuvette holder for use with the apparatus shown in FIG. 1.

An apparatus, indicated generally at 10 in the drawing, embodying the principles of the present invention, includes a sample housing 12, shown in FIG. 2, having a linearly movable sample carrier 14 therein. The housing 12, which is preferably rectangular, is at least equal in length to the sum of the length of a cuvette holder and the length of its maximum displacement.

The linearly movable sample carrier 14 includes a support plate 16 preferably guided on a pair of parallel rails 18 which rails 18 constitute guiding means. The guiding means can be, for example, rollers or other known mechanisms. The support plate 16 is provided with a means 20 for retaining a cuvette holder 22. In the preferred embodiment, the retaining means 20 is a pair of diagonally opposed apertures 24.

The apparatus 10 also includes a support plate advancing mechanism 26 including a leg 28 of a bracket 30 attached with two bentover lugs 32 to one long side of support plate 16 by means of screws 34. The other leg 36 of bracket 30 is attached to a cylindrical rod 38. The cylindrical rod 38 forms part of an advancing means and extends through an aperture 40 in leg 36 and is retained on one side thereof by a washer 42 secured by a snap ring 44 and on another side thereof by a washer secured by a spring 46 supported at a spring collar 48 at the cylindrical rod 38. The housing 12 further includes two blocks 50, 52 projecting from the bottom thereof and having apertures through which the cylindrical rod 38 is guided. The first block 50 is located close to the narrow side of the housing 12, through which side the cylindrical rod 38 is light-tightly passed in conventional manner.

The second block 52 is located at a distance therefrom beyond the center of the housing 12 and includes an aperture 54 aligned to the aperture in block 50 having a bore extending normally thereto which is closed by an adjusting screw 56. Preferably, a spring-loaded ball is positioned in the bore for purposes described hereinbelow.

The cylindrical rod 38 is provided with annular grooves 58 formed at the free end thereof projecting from block 52, the distance of the grooves 58 correspond to the distance of the cuvettes in the cuvette holder 22. The displacement of cylindrical rod 38 is preferably limited, on one end, by the abutment of snap ring 44 to the second block 52 and, on the other end, by the abutment of spring collar 48 to the first block 50. The end of cylindrical rod 38 outside of the housing 12 is provided with a knob 60 by means of which the cylindrical rod 38 can be manually displaced in the longitudinal direction of the housing 12. Alternatively, a motorized advancing means can be provided, for example, a rack driven by a pinion or a band guided and driven by rollers connected to leg 36 of bracket 30, with suitable locking means, sensors for the angle of rotation etc. being provided to limit the advance to the respectively desired amount.

Referring particularly to FIG. 2, there is shown a first embodiment of a cuvette holder 22 for retaining a plurality of samples. A wall 62, forming part of the cuvette housing 12, includes an entrance window 64 through which passes the excitation radiation and an exit window 66 through which passes the fluorescence radiation. Preferably, the cuvette holder 22 includes a rectangular base plate 68 having a plurality of cuvette receptacles 70 projecting perpendicularly therefrom to receive the cuvettes, each receptacle 70 being provided with an entrance aperture 72 and an exit aperture 74, which apertures, 72 and 74, face the wall 62. Each receptacle 70 is sized to receive a rectangular cuvette 76.

Figure 3:
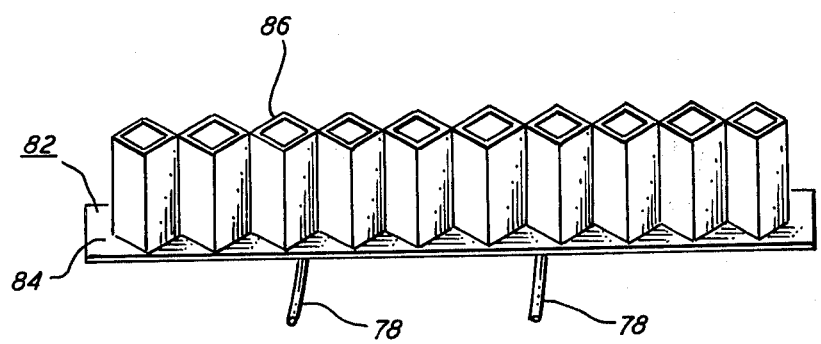
FIG. 3, which is a perspective view of another embodiment of a cuvette holder useful with the apparatus shown in FIG. 1.

Preferably, the base plate 68 is provided with pins 78, shown in FIG. 3, which protrude from the underside thereof. The pins 78 function as retaining elements which engage apertures 24 on the support plate 16 of the carrier 14 to secure the cuvette holder 22 thereto.

Figure 1:
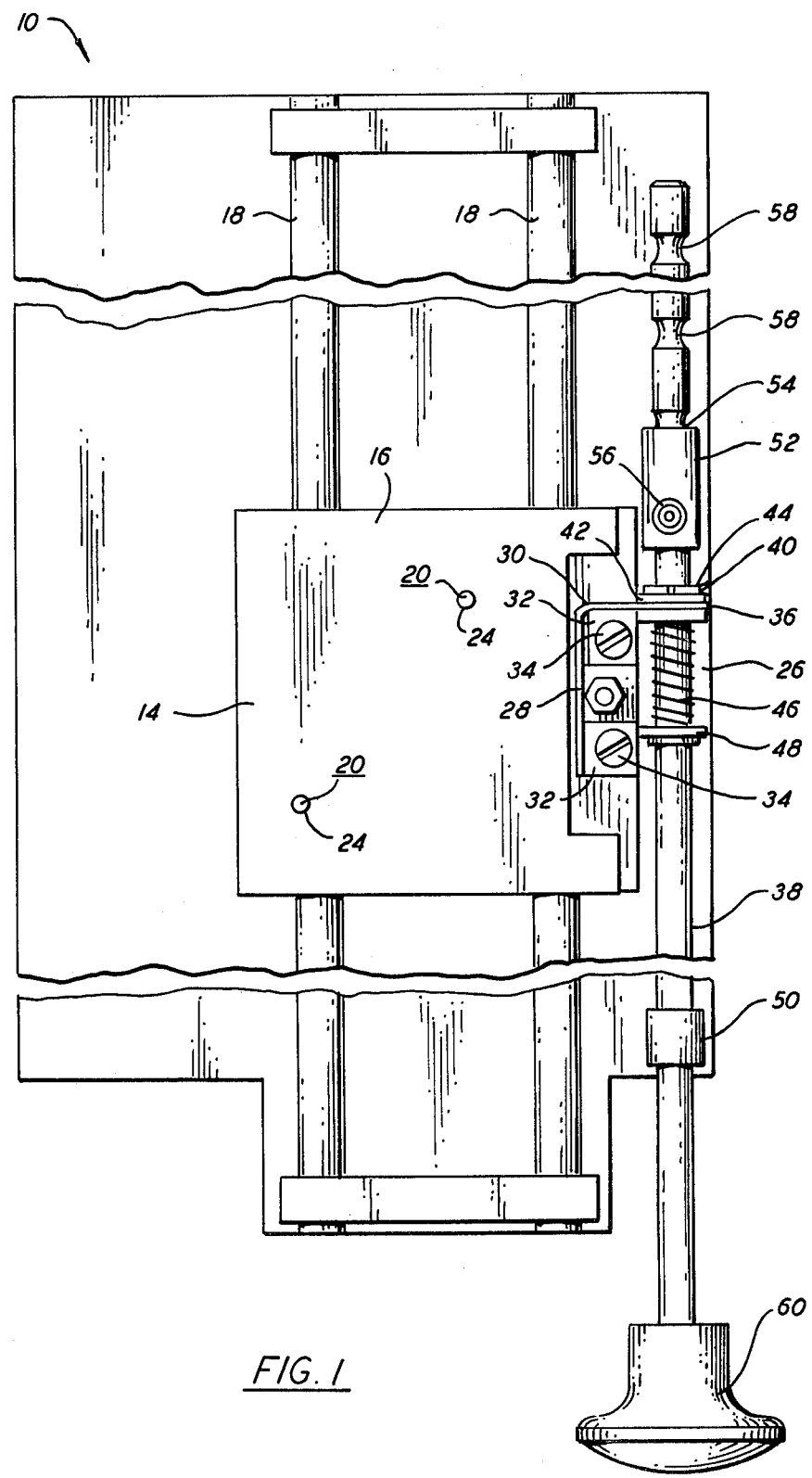
FIG. 1, which is a plan view of an apparatus embodying the principles of the present invention.

With the cylindrical rod 38 locked in its initial position, the spring collar 48 is located close to block 50, and a first cuvette receptacle 80 is positioned in a measuring position. In the terminal position, as shown in FIG. 1, leg 36 of bracket 30 is positioned close to block 52 and the last cuvette receptacle 81 on base plate 68 is in the measuring position. The pins 78 and the apertures 24 are preferably arranged such that base plate 68 can only be placed on support plate 16 in such a way that the entrance aperture 72 faces the entrance window 64, and the exit aperture 74 faces the exit window 66.

FIG. 2 shows the fluorescence radiation emitted normally with respect to the direction of the exciting radiation in dashed lines; the fluorescence radiation enters the fluorimeter through the housing 12 exit aperture 74 and exit window 66, in which fluorimeter, for instance, the intensity of the total emission or its spectral distribution over a wider or smaller wavelength range is measured.

Advantageously, the base plate 68 or the cuvette receptacles 70 may be designed with double walls and connected to a circulating thermostat. Such an arrangement is well known in the art and need not be described in detail herein.

FIG. 3 depicts another embodiment of a cuvette holder 82 made of a sufficiently transparent plastic for radiation in the range of the investigation. The cuvette holder 82 is preferably formed integrally with the cuvettes and is designed to be used only once. The cuvette holder 82 consists of a rectangular base plate 84 provided with a plurality of cuvette holders 86 projecting therefrom which are disposed diagonally with respect to the longitudinal direction of base plate 84 and are diagonally interconnected. Base plate 84, similar to base plate 68, is also provided with pins 78 protruding from the underside thereof, which pins 78 are adapted to engage apertures 24 on support plate 16. In this embodiment, the cuvette holder thermostatting may also be provided by designing support plate 16 with double walls and by connecting the same to a circulating thermostat. Alternatively, clamps may be provided instead of the pins to secure the base plate 84 to the support plate 16.

The fluorimeter sampling apparatus described hereinbefore, particularly the one having the cuvette arrangement as shown in FIG. 3, may be readily combined with apparatus for preparing and processing samples as known in clinical chemistry for automatic series investigations (R. Haeckel; Rationalisierung des medizinischen Laboratoriums; GIT-Verlag Ernst Giebeler, Darmstadt 1976).

While the present invention has been described herein with respect to specific embodiments, it will be apparent to those skilled in the art that such description is considered exemplary and is not deemed limiting. Hence, the scope of the present invention is defined by the appended claims and the reasonable interpretation thereof.

What is claimed is:

1. A fluorimeter sampling apparatus comprising:
   a sample housing;
   a movable carrier positioned within said sample housing, said carrier being adapted to move linearly along guiding means therein;
   a support plate having means for retaining a cuvette holder, said support plate being releasably attached to said carrier, said cuvette holder having a plurality of generally rectangularly-shaped cuvette receptacles extending therefrom, said receptacles being arranged diagonally with respect to the direction of linear movement of said carrier, each said receptacle having an entrance aperture adapted to accept and pass therethrough excitation radiation and an exit aperture adapted to pass fluorescence radiation therethrough, said entrance and exit apertures being positioned on adjacent sides of each said receptacle.

2. Apparatus as claimed in claim 1 wherein said sample housing comprises:
   an entrance window through which excitation radiation can be directed upon said receptacle;
   an exit window through which fluroescense radiation can be directed from said receptacle; and
   said entrance window and said exit window being aligned with said entrance aperture and said exit aperture, respectively, when said receptacle is in a measuring position.

3. Apparatus as claimed in claim 1 wherein:
   said cuvette receptacles and said cuvette holder are a single integral unit.

4. Apparatus as claimed in claim 3 wherein said unit is transparent to said excitation radiation and said fluorescence radiation.

* * * * *